United States Patent [19]

Takatori et al.

[11] Patent Number: Plant 5,317

[45] Date of Patent: Oct. 30, 1984

[54] ASPARAGUS PLANT—F189

[75] Inventors: Frank H. Takatori; Franklin D. Souther, both of Riverside, Calif.

[73] Assignee: The Regents of the University of California, Berkeley, Calif.

[21] Appl. No.: 468,015

[22] Filed: Feb. 18, 1983

[51] Int. Cl.[3] ..... A01H 5/12

[52] U.S. Cl. ..... Plt./89

[58] Field of Search ..... Plt./89

*Primary Examiner*—Robert E. Bagwill

*Attorney, Agent, or Firm*—Townsend and Townsend

[57] ABSTRACT

A new and distinct variety of female asparagus plant characterized by its erect growth to a height greater than six feet, its ability to produce an average of 25 to 27 stalks per plant and by its high branching (the first lateral branching occurs about 15 inches above soil level). The plant of the variety contains a gene which it imparts to its progenies and is expressed by the distinguishing characteristic known as "tip" flowers.

3 Drawing Figures

DESCRIPTION

This invention relates to a new and distinct female clone of asparagus designated as F189. Plant F189 was selected from a line designated as S102 which was an open pollinated cross of female plant designated as F111, variety UC66, which was planted at the University of California Agricultural Experiment Station, Moreno, Calif., in 1964. The source of seed for the UC66 planting was obtained from Mr. J. Hanna, formerly a member of the Department of Vegetable Crops, University of California, Davis, Calif.

Female plant F189 is a vigorous growing, large-speared plant that grows erect to a height exceeding six feet and in all production areas will be larger than male plant M138. An established F189 plant three years of age or older will produce an average of 25 to 27 stalks per plant per year. The stalks measured at soil level will average between 1¼ and 1 ¾ inches in diameter.

Plant growth is erect, and the foliage referred to as fern is dark green (Plate XVIII) in color. The first lateral branch occurs about 15.0 inches above the soil level and exhibits a plant characteristic referred to as high branching.

The female plant F189 carries the genes that transmit to its progeny a flowering characteristic designated as "tip" flowers, where the first flower is initiated at the terminal end of a cladophyll on the fourth to sixth spear to emerge after planting, rather than at the axil along the stems as in other commercial varieties. This characteristic is a particularly distinguishing one when compared to other known varieties of asparagus plants.

Asparagus is a dioecious plant, individual plants being either male or female in sex.

Figure 1:
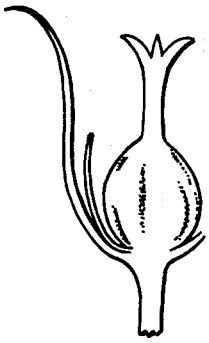
FIG. 1 shows the typical female parts of F189.
Figure 2:
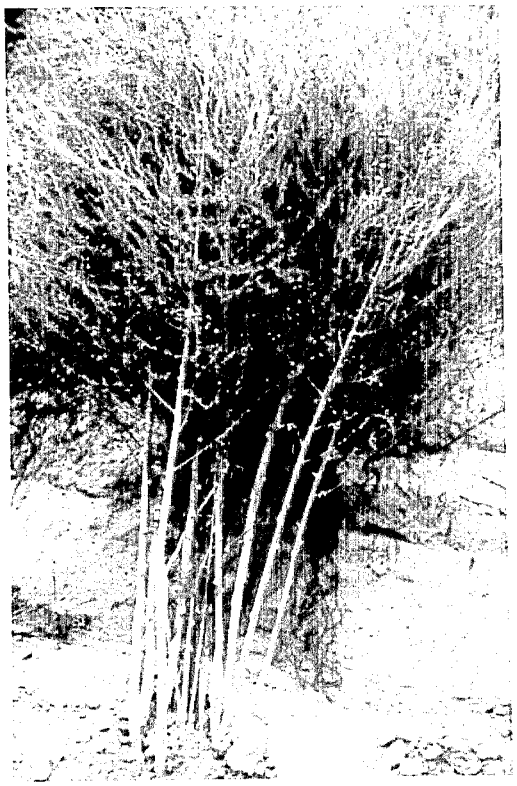
FIG. 2 shows the large-sized stalks, erect growth, and high-branching characteristic of the plant.
Figure 3:
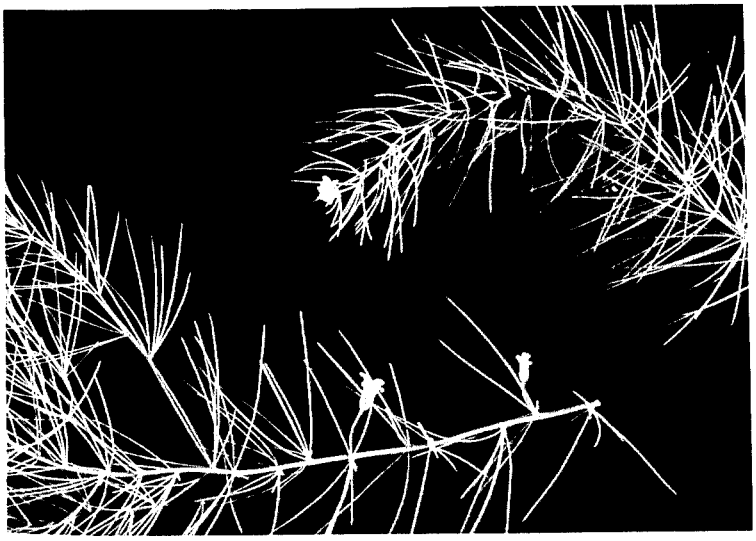
FIG. 3 shows a "tip flower" characteristic of progenies produced when F189 is the female parent of any cross.

The only existing methods of asexual reproduction of asparagus plants for the multiplication of plants of this invention are crown divisions or tissue culture. The plant of this invention has been asexually reproduced by tissue culture techniques, which are more conductive to large-scale multiplication of asparagus plants than is crown division.

The colors designated hereinafter are approximate and may vary with several factors including soil type, nutrition, temperature, and maturity. The colors have been determined by comparison to the colors in "Color Standard and Color Nomenclature" by Robert Ridgway, Washington, D.C., 1912.

PLANT CHARACTERISTICS

Spear: Straight, smooth and round with slow taper terminating in a tight compact head. Spear color is Biscay Green (Plate XVII). Bracts covering nodes, Lumiere Green (Plate XVII) in color, tightly adhering to the spear. Lateral branches are initiated from the twelfth node when the spears are 15 to 16 inches in height. Emergence in the spring is early.

Foliage: An erect perennial herb Light Bice Grren (Plate XVII) during growth which turns Varley Green (Plate XVIII) as it matures. The stalks are straight with many lateral branches above the twelfth node. The latent buds below the twelfth node initiate lateral branches as the stalk reaches maturity. A three-year-old or older plant will develop an average of 25 to 27 stalks, 1½ inches (average) in diameter, that grow to a height in excess of six feet. The mature cane is Turtle Green (Plate XXXII), and the bracts are Orchraceous Buff (Plate XV) in color.

Asparagus does not possess true leaves; the leaf-like structures are called cladopohylls. Both cladophylls and stalks provide photosynthetic "leaf area".

Inflorescence: One to four, usually two in axil with cladodes. Flowers (0.5 to 0.6 cm length) and Light Greenish Yellow (Plate V) companulate, with rudimentary, nonfunctioning stamens.

Fruit: Diameter 0.8 to 0.85 cm average diameter, with color changes from Biscay Green (Plate XVII) (immature) to Sayal Green (Plate XXIX) to Scarlet (Plate I) at maturity. Seed number varies from 1 to 9 per berry.

Crown-root: Crown a woody rhizome with long fleshy storage roots and fibrous absorptive roots originating from the fleshy storage roots. Storage roots numerous, ¼ to ⅜ inches in diameter and extending five to ten feet in all directions.

We claim:

1. The new and distinct variety of asparagus plant herein described and illustrated and identified by the characteristics enumerated above.

* * * * *